United States Patent [19]
Jacobs

[11] 3,957,048
[45] May 18, 1976

[54] INTRAVENOUS DEVICE

[76] Inventor: Herbert V. Jacobs, The Philadelphian, Apt. 18BB31, 2401 Pennsylvania Ave., Philadelphia, Pa. 19130

[22] Filed: Nov. 20, 1974

[21] Appl. No.: 525,415

Related U.S. Application Data

[63] Continuation-in-part of Ser. No. 511,893, Oct. 3, 1974, abandoned.

[52] U.S. Cl............................ 128/214 R; 128/133; 128/DIG. 26
[51] Int. Cl.².......................................... A61M 5/32
[58] Field of Search.......... 128/214 R, 214.2, 214.4, 128/215, 216, 221, 133, DIG. 26, 347

[56] References Cited
UNITED STATES PATENTS

| | | | |
|---|---|---|---|
| 1,213,001 | 1/1917 | Philips | 128/347 |
| 2,402,306 | 6/1946 | Turkel | 128/215 |
| 2,409,432 | 10/1946 | Hubbard | 128/133 |
| 2,589,426 | 3/1952 | Ogle | 128/216 |
| 2,899,959 | 8/1959 | Ginsburg | 128/221 |
| 3,734,095 | 5/1973 | Santomieri | 128/214.4 |
| 3,834,380 | 9/1974 | Boyd | 128/133 |

Primary Examiner—Dalton L. Truluck
Attorney, Agent, or Firm—Caesar, Rivise, Bernstein & Cohen, Ltd.

[57] ABSTRACT

An intravenous feeding device including a hollow feeding needle having a right angle bend at the end removed from the feeding tip. A length of plastic tubing is connected to the remote end of the needle and extends through a post. The post is secured to a strap arranged for securement to the patient. The post and associated strap can be moved with respect to the needle to enable the strap to be positioned in contact with the patient for securement thereto when the feeding end of the needle is disposed centrally within the vein of the patient. A thumb screw is provided in the post to secure the needle in place once the needle is in position. All of the foregoing functions immobilize the needle so it can not be moved or pulled away from its proper position.

7 Claims, 5 Drawing Figures

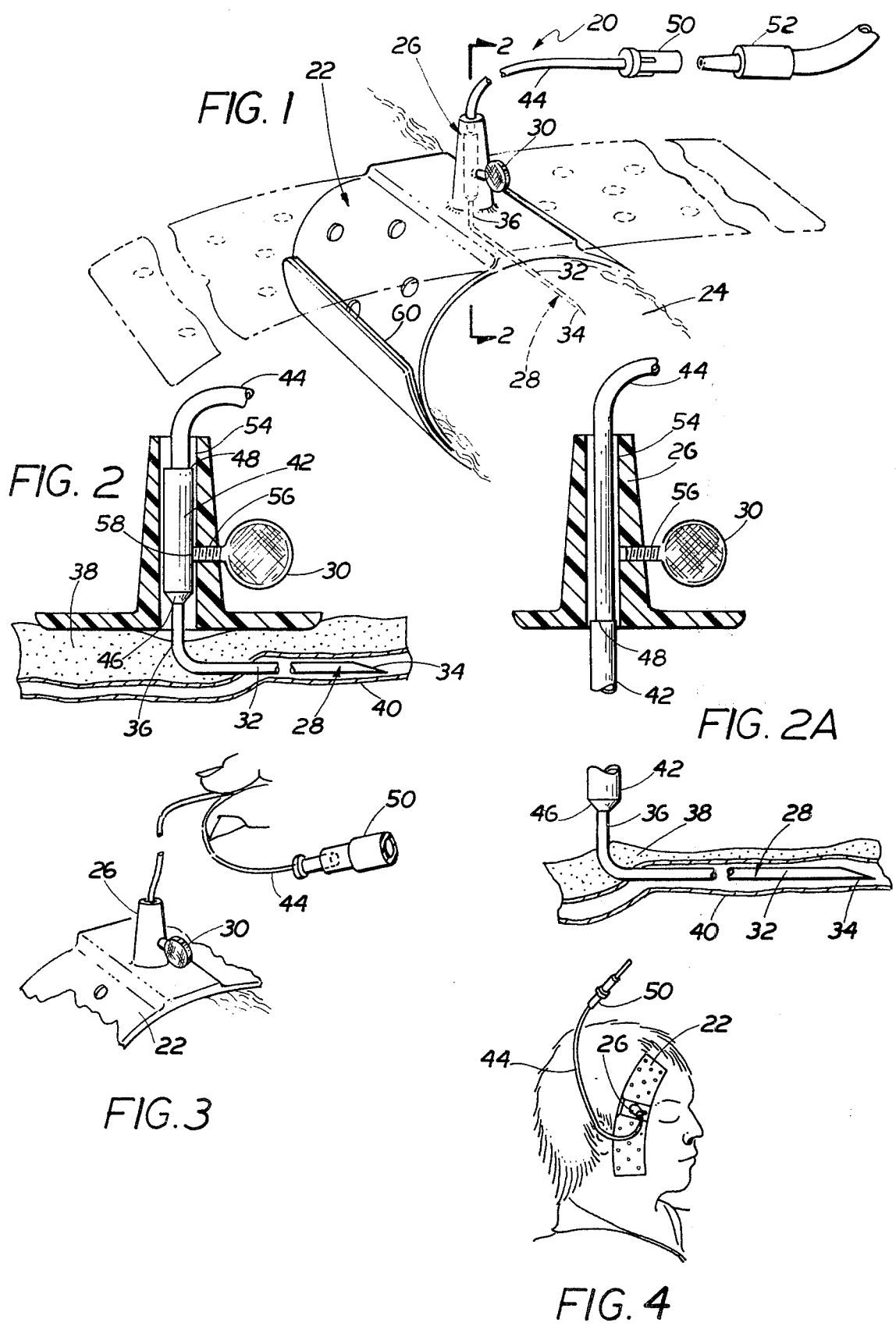

INTRAVENOUS DEVICE

This application is a continuation-in-part of U.S. patent application Ser. No. 511,893, filed on Oct. 3, 1974, now abondoned, whose disclosure is incorporated by reference herein.

This invention relates generally to medical devices and more particularly to intravenous feeding devices.

Various techniques and apparatus are presently employed for the purpose of intravenous feeding of various fluids to a patient. The most common technique utilizes infusion apparatus including a straight needle, a handle portion and a length of tubing for connecting the needle to a source of intravenous fluid. The needle is inserted into the vein of the patient and is secured in position with adhesive tape connected to the handle.

Unfortunately, in utilizing such a technique, the needle remains substantially exposed and can be readily loosened or inadvertently removed.

Several intravenous feeding devices have been described in patent literature for effecting the immobilization of the intravenous needle wihin the vein of the patient. For example, U.S. Pat. Nos. 2,077,774, 2,266,231, 2,821,194, 3,046,984, 3,064,648, 3,538,915, 3,722,508, and 3,782,378, However, all of such devices suffer from one or more of various disadvantages, e.g., efficacy, complexity, cost, comfort, etc.

In addition, since heretofore all prior art intravenous feeding devices utilize a straight needle, in order to insert the needle in through the flesh of the patient and into the underlying vein, the needle is necessarily inserted at an acute angle with respect to the vein. The angular disposition of the needle with respect to the vein renders the needle susceptible to accidentally piercing entirely through the vein and entering the underlying tissue. The result of such an occurence is that the intravenous fluid infiltrates the surrounding tissue of the patient. Such infiltration can be extremely painful and in addition, during such action, since the fluid is entering the surrounding tissue and not the vein, the patient is deprived of the essential fluid.

It is a general object of this invention to overcome the various disadvantages of the prior art.

It is a further object of this invention to provide an intravenous feeding device including a needle which can be readily inserted centrally within the vein of the patient and once inserted can be immobilized therein.

It is still a further object of this invention to provide an intravenous feeding device having a feeding needle which can be positioned centrally within the vein of the patient and irrespective of the depth at which the vein is located under the skin of the patient.

These and other objects of this invention are achieved by providing an intravenous feeding device comprising strap means for securement to the user, post means fixedly secured to the strap and a feeding needle. The feeding needle includes a main portion having a pointed end and a remote portion extending at angle to the main portion, the compliment of which angle is substantial, e.g., 20° to 90°. The needle is freely positionable with respect to the post to enable the main portion thereof to be located centrally within the vein of the user, with the strap secured to the user. The device also includes releasable securement means for securing the needle with respect to the post once the needle and the strap means are in position.

Other objects and many of the attendant advantages of this invention will be readily appreciated as the same becomes better understood by reference to the following detailed description when considered in connection with the accompanying drawings wherein:

FIG. 1 is a perspective view of the intravenous feeding device when secured to the arm of the patient;

FIG. 2 is an enlarged sectional view taken along line 2—2 of FIG. 1;

FIG. 2A is an enlarged sectional view of a portion of the feeding device at an intermediate step in the securement of the device to the patient;

FIG. 3 is a perspective view of a portion of the intravenous feeding device of this invention shown in the manner that the device, once connected to the patient, can be secured to any intravenous fluid supply; and FIG. 4 is an elevational view of the device of this invention when secured onto the head of the patient for the introduction of intravenous fluid into a vein therein.

Referring now to the various figures of the drawing wherein like reference characters refer to like parts, there is shown in FIG. 1 an improved intravenous feeding device 20. Device 20 basically comprises a strap 22 for securement to the user's body, such as arm 24 of the user, a post 26 fixedly secured to strap 22, an intravenous feeding needle 28 and securement means 30 for fixing the position of the needle with respect to the strap 22 and post 26.

The feeding needle 28 is an elongated tubular member for carrying an infusion fluid, and in the interest of hygiene is preferably formed of stainless steel, as can be seen clearly in FIGS. 2 and 2A the needle includes a main portion 32 terminating at its free end in a pointed tip 34 and a remote portion 36. The remote portion 36 is formed integrally with the main portion 32 and in accordance with the preferred embodiment which is shown in the drawing herein extends at a general right angle with respect thereto. It should be pointed out at this juncture that while the angle between the remote portion of the needle is shown as being 90°, it is clear that this invention contemplates different angular orientations between said portions. For example, this invention contemplates that the remote and main portions can be at an angle whose compliment is substantial, e.g., between 20° and 90°, and will accomplish the ends sought, e.g., the preclusion of infiltration. By utilizing a needle whose main portion is so angularly related to the remote portion that the compliment of said angle between he two portions lies in the range of 20° to 90° the needle 28 is particularly suitable for penetrating through the flesh of the user into the underlying vein 40, with the main portion 32 of the needle extending within the vein and along the center axis thereof and with the remote portion extending outward and through the flesh of the user at a substantial angle thereto to provide a freely accessible entrance port for the infusion fluid.

A coupling member 42 is connected between the remote end 36 of the needle 28 and a flexible infusion fluid carrying conduit 44. To that end the coupling 42 is a tubular member having a tapered end 46, a flat end 48 and a central passageway (not shown) extending between said ends such that when connected the fluid flowing through conduit 44 passes through coupling 42 and into the needle 28 for infusion into the vein of the patient. The conduit 44 terminates at its free end in a conventional releasable, universal coupling 50 adapted for connection to a conventional outlet 52 of an intravenous feeding supply (not shown), such as a bottle of 5% glucose solution.

The coupling 42 is formed of a rigid material, such as rigid plastic, and is arranged for disposition within a longitudinal, central opening 54 in post 26. In order to accomodate the remote portion of the needle within opening 54, the post projects upward from the strap at the angle which is the compliment of the angle between the main and remote portions of the needle (i.e., 90° in the embodiment shown in the drawings but within the range of 20° to 90°).

As can be seen in FIG. 2, the opening 54 is of a greater diameter than the outside diameter of the coupling 42 such that the coupling is freely movable longitudinally therein. This feature is of significant importance in that it permits the precise placement of the needle within the vein without an interference from the strap and the post associated therewith. Once in proper position within the vein, the securement means 30, which is in the form of a thumb screw threaded through an opening 56 in the sidewall of the post 26, is tightened, thereby causing the end 58 of the thumb screw to tightly abut the rigid coupling to secure it in place with respect to the post.

In accordance with the preferred embodiment of this invention, the strap 22 includes an adhesive coating 60 on its underside to enable the strap to be firmly secured to the user, such as by wrapping around the arm 24, as shown in FIG. 1, or by being applied in a generally flat manner, as shown in FIG. 4. Of course, it is to be understood that various means, e.g., buckles, VELCRO strips, adhesive tape, etc., could be used to effect the securement of the strap to the patient.

Operation of the device 20 can best be understood by reference to FIGS. 1, 2 and 2A.

With the thumb screw 30 loosened such that coupling 42 is extended out of opening 54 in post 26, the pointed tip 34 of the needle is inserted by the physician through the flesh 38 of the patient and into the vein 40. Since the main portion 32 of the needle is at a right angle to the remote portion, the main portion of the needle is enabled to be moved along the vein to extend sufficiently therein. Once the needle is in the vein, the physician lowers the post and associated strap, from the position shown in FIG. 2A, and into contact with the skin, as shown in FIG. 2. The strap 22 is then wrapped, from its phantom line position, shown in FIG. 1, to the solid line position shown therein to contact the skin of the patient. The tacky adhesive surface 60 immobilizes the strap and post with respect to the patient.

The physician then moves the coupling 42 toward and away from the patient in order to gauge the diameter of the vein to effect the precise placement of the main portion 32 at an equal distance between the top wall and bottom wall of the vein. The physician then rotates the coupling about its longitudinal axis to gauge the width of the vein so as to enable the tip of the needle to be positioned precisely along the central axis of the vein. The physician then tightens the thumb screw to effect the securement of the needle with respect to the post. This action, in effect, immobilizes the needle within the vein of the patient. The needle thus cannot swing or turn because of the anchoring action of the thumb screw and the adhesively secured strap is also significant for preventing swinging or turning, thereby giving double protection against the movement of the needle.

Once the device 20 is in place, as described immediately above, the universal coupling 50 is connected to port 52 of the fluid supply to start intravenous feeding. In order to prevent the patient's blood from exiting through the device 20 and out of the coupling 50 before the coupling is connected to outlet 52, the flexible conduit 44 is pinched between one's fingers as shown in FIG. 3.

It should be clear that with the use of this invention, the needle is immobilized within the center of the vein and cannot pierce the vein into the surrounding tissue, irrespective of whether or not the device is pulled or bumped. Such action prevents the infiltration of the intravenous fluids into the surrounding tissue of the user, which action frequently occurs with prior art intravenous feeding devices.

Although the post 26 is only shown as including a thumb screw 30, it should be clear that the post could also include a valve(s) for regulating or shutting off the flow of fluid through the conduit 44 and/or for permitting the flow of one or more infusion fluids into the patient at the same time.

While the invention has been heretofore described for intravenous feeding, it should be clear that once the device is in place, it serves as a convenient means for the taking of blood samples from the patient or for giving injections. For example, insofar as the former is concerned, all that is necessary is that the flexible conduit 44 be pinched while the suitable blood sample receptacle is connected, via coupling 50 to the device 20. Once the connection is made, the conduit 44 is released thereby enabling the blood to flow through the needle 28, coupling 42, conduit 44 and into the receptacle. Insofar as the latter is concerned, all that is necessary is that the conduit 44 be pinched and a suitable syringe be inserted within universal connector 50 and thereafter the conduit released and the contents of the syringe injected into the conduit 44 for introduction into the patient.

It should be appreciated from the foregoing that the intravenous feeding device of this invention enables one to make a quick and precise penetration of a feeding needle into the user's vein. Since the needle is freely positionable with respect to the means for securing it in place and since the needle includes a remote portion extending at an angle, whose compliment is substantial, to the vein piercing portion, the needle is enabled to be precisely positioned within the vein without the danger of penetration out through the vein, irrespective of the depth that the vein is disposed below the skin. In addition, the securement means of this invention enables the needle to be immobilized at a precise location within the vein in a simple, effective and secure manner.

Without further elaboration, the foregoing will so fully illustrate my invention that others may, by applying current or future knowledge, readily adapt the same for use under various conditions of service.

What is claimed as the invention is:

1. An intravenous feeding device comprising strap means for securement to the user, post means fixedly secured to the strap means and having a needle receiving opening, a feeding needle including a main portion having a pointed end and a remote portion extending at an angle to the main portion, said needle being removably received within said opening and freely positionable with respect to said post to enable the main portion thereof to be extended a sufficient distance from said strap means and parallel thereto to permit said main portion to be located centrally within the vein of the user when said strap is secured to said user and irrespective of the distance that said vein lies below the skin of said user, and releasable securement means for securing the remote portion of said needle in said opening and with respect to the post once the main portion of said needle is in position within the vein of the user and the strap is secured to the user.

2. The intravenous feeding device of claim 1 wherein the compliment of said angle is between 20° and 90°.

3. The device of claim 2 wherein the angle is approximately 90°.

4. The intravenous feeding device of claim 1 wherein a rigid tube is fixedly secured to the remote portion of said needle and is in fluid communication therewith, said post including an opening through which said tube extends, said opening being of a greater diameter than said tube to enable said tube and the needle secured thereto to be positioned with respect to said post.

5. The intravenous feeding device of claim 4 wherein said releasable securement means comprises a thumb screw for securing said tube with respect to said post.

6. The intravenous feeding device of claim 5 wherein a flexible conduit is connected to said tube and is in fluid communication therewith, said flexible conduit having a universal connector at its free end.

7. The intravenous feeding device of claim 6 wherein said strap means includes an adhesive surface thereon for contact with the body of the user.

* * * * *